United States Patent [19]

Lin et al.

[11] Patent Number: 5,245,105
[45] Date of Patent: Sep. 14, 1993

[54] SEPARATION OF ALUMINUM ALKYLS FROM OLEFINS USING POLYPHENYLENE OXIDE MEMBRANE

[75] Inventors: Kaung-Far Lin; William B. Waites, both of Baton Rouge, La.

[73] Assignee: Ethyl Corporation, Richmond, Va.

[21] Appl. No.: 8,951

[22] Filed: Jan. 26, 1993

[51] Int. Cl.⁵ .................. C07L 7/144; C02F 1/44; B01D 11/00; D01D 61/00
[52] U.S. Cl. ................................ 585/818; 210/637; 210/644; 210/651; 556/187
[58] Field of Search ............... 585/818; 210/637, 644, 210/651; 556/187

[56] References Cited

U.S. PATENT DOCUMENTS

| | | | |
|---|---|---|---|
| 3,149,179 | 9/1964 | Bowden | 260/683.15 |
| 3,617,553 | 11/1971 | Westaway et al. | 210/23 |
| 3,637,885 | 1/1972 | McClaflin | 260/677 A |
| 3,645,891 | 2/1972 | Goldup et al. | 210/23 |
| 5,151,182 | 9/1992 | Perry et al. | 210/500 |

Primary Examiner—Anthony McFarlane
Assistant Examiner—Nhat D. Phan
Attorney, Agent, or Firm—David M. Bunnell

[57] ABSTRACT

A process for separating a mixture of aluminum alkyl and alpha-olefin comprises contacting, under an elevated pressure of at least about 300 psig, an organic solvent stable, polyphenylene oxide-derived membrane with said mixture and recovering as the permeate an alpha-olefin fraction which contains a lower concentration of aluminum alkyl than in the starting mixture.

11 Claims, No Drawings

SEPARATION OF ALUMINUM ALKYLS FROM OLEFINS USING POLYPHENYLENE OXIDE MEMBRANE

FIELD OF INVENTION

The invention relates generally to organic membrane separation processes and more specifically to a process for separating aluminum alkyls, such as triethylaluminum, from $\alpha$-olefins using a polyphenylene oxide-derived membrane.

BACKGROUND OF THE INVENTION

Aluminum alkyls and especially triethylaluminum are used in the so-called Ziegler chain growth process to prepare linear alpha-olefins. The process involves the reaction of triethylaluminum (TEA) and ethylene at temperatures in the range of 200°-500° F. and pressures in the range of 2000 to 5000 psig to yield a mixture of tri-$C_2$-$C_{20+}$ alkylaluminum compounds and $C_2$-$C_{20+}$ olefins. Linear alpha-olefins are then recovered from the alkylaluminum compounds by olefin displacement using ethylene, 1-butene or mixtures thereof as the displacing olefin. Prior to displacement, the ethylene is flashed from the chain growth product and some of the alpha-olefins such as $C_4$-$C_6$ and $C_8$-$C_{12}$ cuts are removed by distillation. Because of the similar boiling points of TEA and 1-dodecene, the $C_8$-$C_{12}$ cut is contaminated with TEA.

The TEA can be removed by hydrolysis but this causes a loss of the expensive TEA starting material. Accordingly, the amount of $C_8$-$C_{12}$ olefins which can be economically removed from the process is limited so as to minimize the loss of TEA. The remaining $C_8$-$C_{12}$ must be recycled thought the process. U.S. Pat. No. 3,149,179 discloses the use of membrane permeation to separate TEA from linear olefins. Preferred members are those selected from synthetically derived plastics which are predominantly hydrocarbon in nature and especially polyethylene. Polyesters are also mentioned. No working example is provided and the process is described in mostly general terms. In fact, we have found that a successful membrane separation of aluminum alkyls and alpha-olefins is difficult to achieve even considering the advances in membrane technology which have occurred in the approximately 30 years since the issuance of the U.S. Pat. No. 3,149,179. We tried membranes based on polysulfones, polyvinyl alcohol, and ethyl acetate unsuccessfully. We have now discovered a process which, by using a polyphenylene oxide-derived membrane at elevated pressures, successfully separates aluminum alkyls from alpha-olefins.

SUMMARY OF THE INVENTION

In accordance with this invention there is provided a process for separating a mixture of aluminum alkyl and alpha-olefin, said process comprising contacting, under an elevated pressure of at least about 300 psig, an organic solvent stable, polyphenylene oxide-derived membrane with said mixture and recovering, as the permeate, an alpha-olefin fraction which contains a lower concentration of aluminum alkyl than in said mixture.

DETAILED DESCRIPTION OF THE INVENTION

Membranes for use in the process of the invention are composite, organic solvent stable membranes which include a crosslinked layer of a polymer derived from polyphenylene oxide type monomers. This layer is supported on an organic solvent stable, porous membrane substrate. For example, a bromomethylated 2, 6-dimethylphenylene oxide polymer (MW 20,000, 3.2 meq/g active bromine) is coated on a microporous polypropylene support and crosslinked by ammonia or an amine. The crosslinked layer is less than about 5 microns in thickness and preferably from about 0.1 to 0.5 micron in thickness. The substrate may be an organic polymer, glass, ceramic, porous metal or carbon having an average pore size in the range of from 1 to 500 mm, preferably 1 to 100 mm and most preferably 2 to 20 mm, and a thickness preferably in the range of from about 10 to 50 microns. Such composite membranes are described, for example, in U.S. Pat. No. 5,151,182, whose teachings are incorporated herein by reference. The membranes are commercially available from Membrane Products Kiryat Weizmann Ltd. The membranes can be self-supporting or can be supported on a porous material such as sintered glass or metal.

The separation process can be conducted in either a batch or continuous mode. Suitable apparatus are commercially available such as the Sepa ST membrane cell from Osmonics, Inc. The cell is a high pressure, low hold-up volume, chemical resistant, stirred cell which can be adapted to operate at pressures of up to about 1,000 psig.

The aluminum alkyl separation process is preferably operated at temperatures from about 0° to 60° C., with higher temperatures providing increased flux. The process is operated at elevated pressures of at least about 300 psig to obtain a good separation over an extended period, and preferably at pressures of from about 600 psig to 1000 psig.

The process can be employed to separate mixtures containing from about 0.1 up to about 80 wt. % aluminum alkyl, and especially trialkylaluminum compounds wherein each alkyl group contains from about 2 to 20 carbon atoms, and preferably from about 0.5 to 30 wt. % aluminum alkyl, and liquid, linear alpha-olefins having from about 2 to 20+ carbon atoms. Typical examples of such a mixture are $C_8$-$C_{14}$ alpha-olefins containing from about 0.5 to 3.0 wt. % triethylaluminum.

The process is further illustrated by, but is not intended to be limited to, the following examples.

EXAMPLE 1

A feed composition of 1.31 wt. % triethylaluminum (0.29 wt. % Al) and 98.69 wt. % 1-decene was placed in contact with a polyphenylene-oxide membrane (Membrane Products MPF-50 membrane) having a surface area of 2.4 inch$^2$ in a membrane cell under a pressure of 320 psig for 52 hours at room temperature. The concentration of triethylaluminum in the permeate was reduced from the amount in the feed solution as shown in Table 1.

TABLE 1

| Time (hours) | Permeate Wt. % TEA | Flux mL/day |
|---|---|---|
| 0 | 0 | 10–15 |
| 6 | 0.68 | 10–15 |
| 23.5 | 1.10 | 10–15 |
| 52 | 1.18 | 10–15 |

EXAMPLE 2

The process of Example 1 was repeated, except that a different polyphenylene-oxide membrane was used (Membrane Products MPF-60 membrane), the pressure was 300 psig, and the average flux was 5 mL/day. The TEA concentration in the permeate was reduced at first but after about 1 week (171.5 hours) the concentration in the permeate was the same as the feed. The pressure was then raised to 700 psig and the concentration of TEA in the permeate was again reduced and the amount of the reduction remained about the same at from 25 to 35% over a period of about one week. This indicates that operation at higher pressures enhances separation. Also, a higher flux was achieved (8.5–14.0 mL/day). The results are given in Table 2.

TABLE 2

| Time (Hours) | Permeate Wt. % TEA |
|---|---|
| 0 | 0 |
| 24 | 0.21 |
| 49.5 | 0.25 |
| 144 | 0.72 |
| 171.5 | 1.31 |
| 192.5 | 0.89 |
| 217.7 | 0.97 |
| 240.5 | 0.89 |
| 314.5 | 0.84 |
| 342.5 | 0.97 |

What is claimed is:

1. A process for separating a mixture of aluminum alkyl and alpha-olefin, said process comprising contacting, under an elevated pressure of at least about 300 psig, an organic solvent stable, polyphenylene oxide derived membrane with said mixture and recovering, as the permeate, an alpha-olefin fraction which contains a lower concentration of aluminum alkyl than in said mixture.

2. The process of claim 1 wherein said pressure is at least about 600 psig and aluminum alkyl is triethylaluminum.

3. The process of claim 1 wherein the process temperature is from about 0° C. to 60° C.

4. The process of claim 1 wherein said mixture contains from about 0.1 to 80 wt. % aluminum alkyl.

5. The process of claim 1 wherein said mixture contains from about 0.5 to 30 wt. % aluminum alkyl.

6. The process of claim 1 wherein said alpha-olefin contains from about 2 to 20 carbon atoms.

7. The process of claim 1 wherein said alpha-olefin is a $C_2$ to $C_{20}$ linear alpha-olefin.

8. The process of claim 1 wherein said alpha-olefin is a mixture of $C_8$ to $C_{12}$ linear alpha-olefins.

9. The process of claim 1 wherein said alpha-olefin is a mixture of two or more $C_2$ to $C_{20}$ linear alpha-olefins.

10. The process of claim 2 wherein said mixture is derived from an ethylene chain growth process and comprises a mixture of $C_8$ to $C_{12}$ linear alpha-olefins containing from about 0.5 to 3.0 wt. % triethylaluminum.

11. The process of claim 1 wherein said mixture is derived from an ethylene chain growth process and comprises a mixture of $C_2$ to $C_{20}$ linear alpha-olefins containing up to 80 wt. % aluminum alkyl.

* * * * *